US011585706B2

(12) United States Patent
Hayes

(10) Patent No.: US 11,585,706 B2
(45) Date of Patent: Feb. 21, 2023

(54) GUIDEWIRE WITH FIBER BRAGG GRATING STRAIN SENSORS

(71) Applicant: Lake Region Manufacturing, Inc., Chaska, MN (US)

(72) Inventor: John Michael Hayes, Cork (IE)

(73) Assignee: Lake Region Manufacturing, Inc., Chaska, MN (US)

( * ) Notice: Subject to any disclaimer, the term of this patent is extended or adjusted under 35 U.S.C. 154(b) by 0 days.

(21) Appl. No.: 17/492,846

(22) Filed: Oct. 4, 2021

(65) Prior Publication Data

US 2022/0113204 A1    Apr. 14, 2022

Related U.S. Application Data

(60) Provisional application No. 63/091,702, filed on Oct. 14, 2020.

(51) Int. Cl.
| *G01L 1/24* | (2006.01) |
| *A61B 34/20* | (2016.01) |
| *G02B 6/44* | (2006.01) |

(52) U.S. Cl.
CPC ............ *G01L 1/246* (2013.01); *A61B 34/20* (2016.02); *G01L 1/243* (2013.01); *G02B 6/441* (2013.01); *A61B 2034/2061* (2016.02)

(58) Field of Classification Search
CPC ......... G01L 1/246; G01L 1/243; A61B 34/20; A61B 2034/2061; A61B 2017/00084; A61B 2017/00402; A61B 2017/22042; A61B 2090/064; A61B 2090/065; A61B 17/22; G02B 6/441
See application file for complete search history.

(56) References Cited

U.S. PATENT DOCUMENTS

| 7,497,853 | B2 | 3/2009 | Fischer et al. |
| 7,553,305 | B2 | 6/2009 | Honebrink et al. |
| 7,588,555 | B2 | 9/2009 | Pudelko et al. |
| 7,615,044 | B2 | 11/2009 | Scheibe et al. |
| D612,044 | S | 3/2010 | Scheibe |
| D638,934 | S | 5/2011 | Kimmel |
| 7,955,314 | B2 | 6/2011 | Fischer et al. |
| 8,007,463 | B2 | 8/2011 | Pudelko et al. |
| 8,048,026 | B2 | 11/2011 | Fischer et al. |
| 8,048,063 | B2 | 11/2011 | Aeby et al. |
| 8,056,207 | B2 | 11/2011 | Honebrink et al. |
| D653,335 | S | 1/2012 | Kampa et al. |

(Continued)

*Primary Examiner* — John Bedtelyon

(74) *Attorney, Agent, or Firm* — Michael F. Scalise

(57) ABSTRACT

A guidewire including an optical fiber containing three fiber cores, each supporting a strain-sensing fiber Bragg grating (FBG) is described. The three FBGs are susceptible to changes in strain so that axial and lateral force vectors imparted to the FBGs can be ascertained. An optical connector detachably connects the guidewire optic fiber to a proximal optical fiber. The proximal optical fiber in turn is connected to a controller, which in addition to ascertaining the axial and lateral force vectors imparted to each of the FBGs, is programmed to calculate the spatial orientation of the guidewire as it is advanced through the vasculature. This capability is extremely useful for positioning the guidewire at a body site of interest prior to performing a medical procedure. A temperature-sensing FBG is used to compensate for changes in the ambient temperature.

22 Claims, 11 Drawing Sheets

(56) References Cited

U.S. PATENT DOCUMENTS

| | | | |
|---|---|---|---|
| D653,337 S | 1/2012 | Kampa et al. | |
| 8,308,659 B2 | 11/2012 | Scheibe et al. | |
| 8,444,626 B2 | 5/2013 | Fischer et al. | |
| 8,540,697 B2 | 9/2013 | Honebrink et al. | |
| 8,790,362 B1 | 7/2014 | Kimmel et al. | |
| 9,149,607 B2 | 10/2015 | Scheibe et al. | |
| 11,086,073 B2 * | 8/2021 | Hayes | G02B 6/4415 |
| 2009/0177095 A1 | 7/2009 | Aeby et al. | |
| 2016/0128768 A1 | 5/2016 | Leo et al. | |
| 2017/0196479 A1 | 7/2017 | Liu et al. | |
| 2018/0085158 A1 | 3/2018 | Aeby | |
| 2018/0154129 A1 | 6/2018 | Paul et al. | |
| 2018/0206937 A1 * | 7/2018 | Leo | A61B 90/96 |
| 2018/0339134 A1 | 11/2018 | Leo | |
| 2019/0038228 A1 | 2/2019 | Daly et al. | |
| 2019/0374282 A1 | 12/2019 | Tegg et al. | |
| 2020/0238051 A1 | 7/2020 | Hwang et al. | |
| 2021/0052320 A1 | 2/2021 | Holmberg | |

* cited by examiner

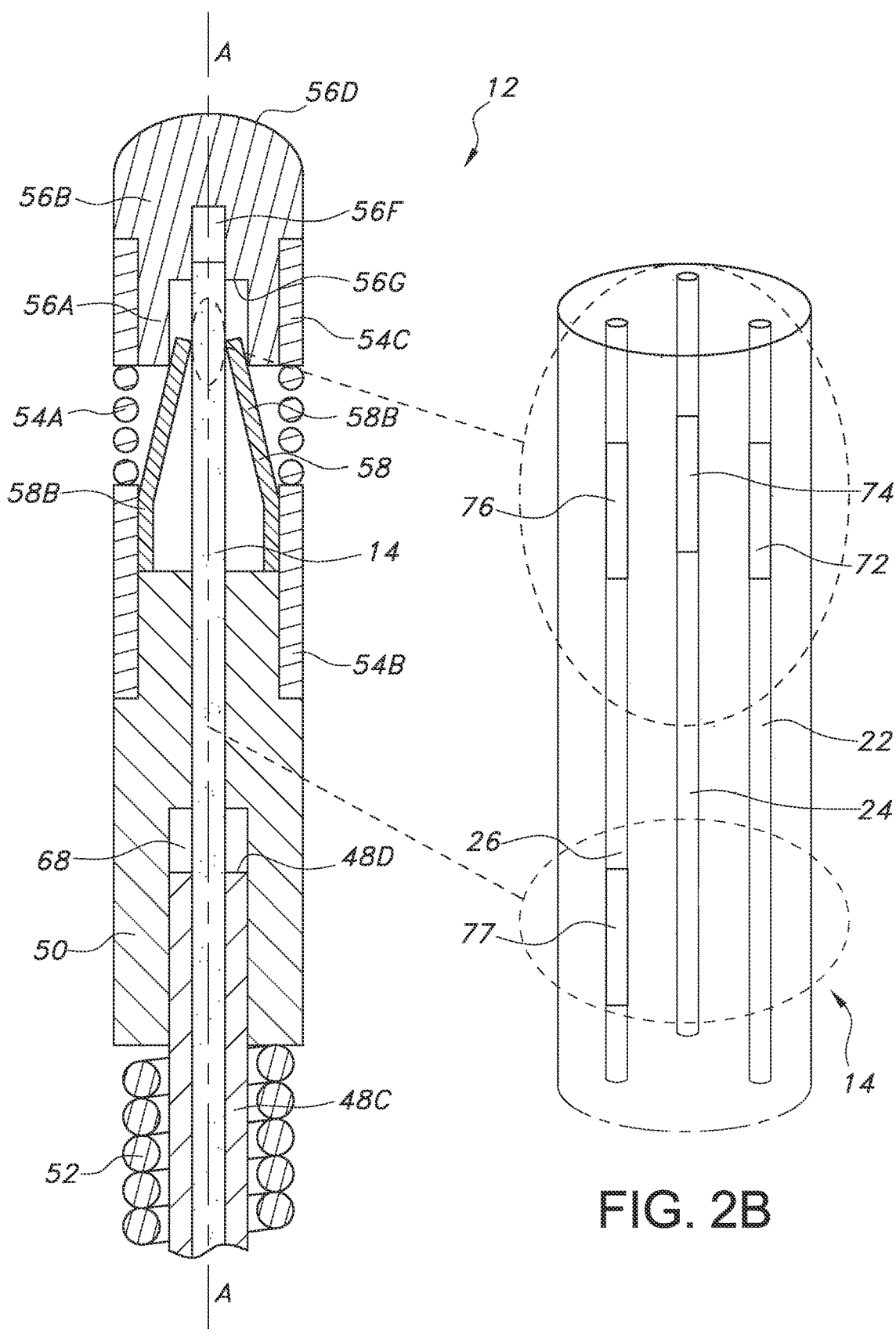

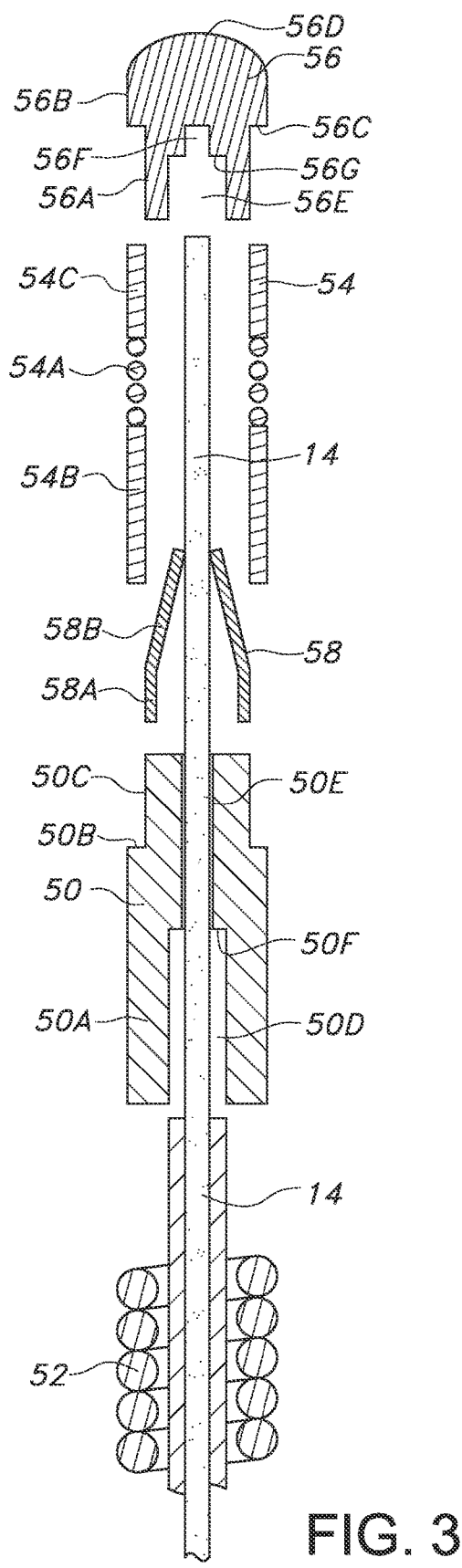
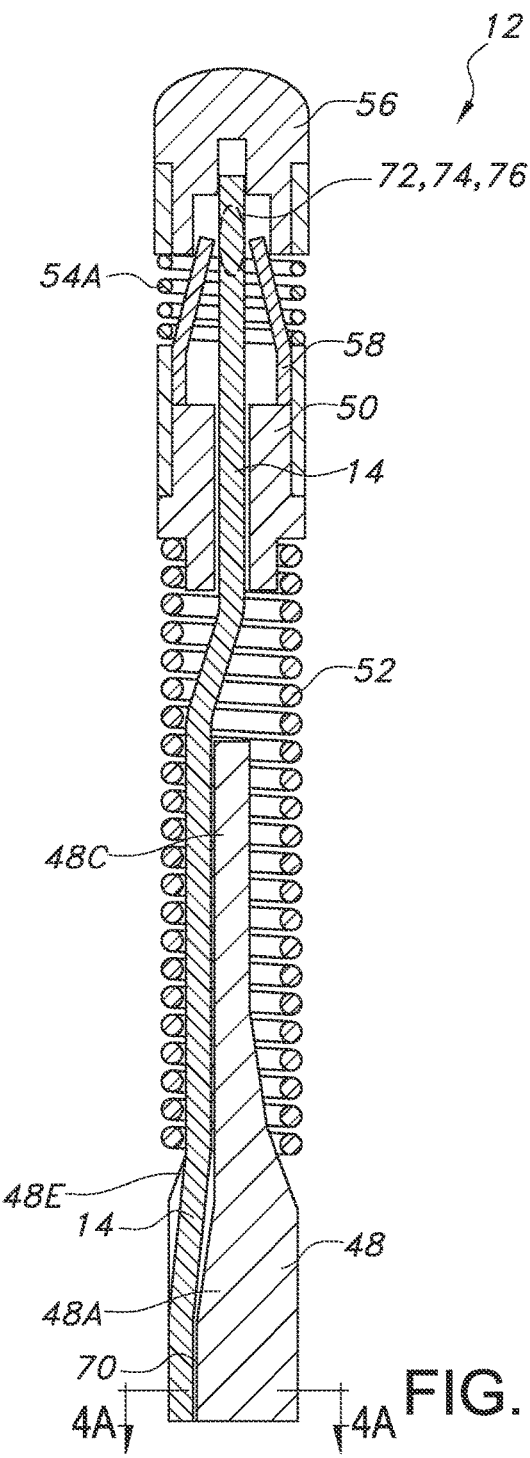
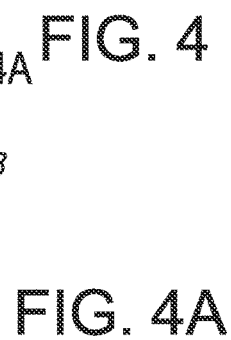
FIG. 3
FIG. 4
FIG. 4A

GUIDEWIRE WITH FIBER BRAGG GRATING STRAIN SENSORS

CROSS-REFERENCE TO RELATED APPLICATION

This application claims priority to U.S. Provisional Application Ser. No. 63/091,702, filed on Oct. 14, 2020.

BACKGROUND OF THE INVENTION

1. Field of the Invention

The present invention relates to the field of medical devices, and specifically to a guidewire for treating a medical condition in a patient. An exemplary medical condition is the treatment of an occlusion attributed to atherosclerosis.

2. Prior Art

Atherosclerosis is the narrowing or occlusion of an artery due to a build-up of plaque and is the most common cause of cardiovascular disease. Occlusions result in impaired blood flow in an artery, which can cause angina, heart attack, heart failure, limb impairment, or limb loss.

To diagnose and treat arteriosclerosis, a guidewire is inserted into the vascular system of a patient through an accessible artery such as the femoral artery. Then, the guidewire is moved through the vasculature to the occluded vessel area. Navigation of the guidewire can be achieved by rotating its external proximal end while pushing forward. The position of a conventional guidewire is typically visualized by 2D x-ray imaging with contrast fluid. Diagnostic and treatment catheters are then delivered over the guidewire to the diseased area.

During forward steering of the guidewire, frictional feedback from the surface of the shaft of the guidewire dominates the tactile feel in the surgeon's hand while tactile perception of the force acting at the atraumatic head is minimal. The lack of tactile perception at the atraumatic head presents a risk of vessel injury such as perforation due to the force of the guidewire head against vasculature tissue.

SUMMARY OF THE INVENTION

To overcome the shortcomings of conventional guidewires, a guidewire according to the present invention has an optical fiber containing force sensors positioned adjacent to the distal atraumatic head. The sensors feed force data imparted to the atraumatic head back to a controller or computer that is programmed to calculate the orientation in an x, y, z coordinate system of the guidewire in the vasculature and present that data on a visual display. If desired, the controller also uses the force data at the atraumatic head to generate an input signal to an electromechanical vibrator integrated into the guidewire's optical connector so that the surgeon receives force feedback at the hand. A temperature sensor in the optical fiber is used to compensate the force data for changes in temperature outside and inside the vasculature.

This increased feedback to the surgeon helps reduce the risk of damaging vasculature tissue, speeds up medical procedures and reduces contrast fluid and x-ray use. Also, the force sensor data correlates with the hardness of tissue encountered by the guidewire so that the occlusion orientation can be determined precisely, thereby reducing the x-ray requirement further. The force data at the occlusion also gives information to the surgeon regarding the makeup of the blockage such as how calcified it is. This type of information is useful in helping the surgeon make treatment decisions such as whether to insert a stent, or not.

Briefly, a guidewire according to the present invention has a hypotube connected to the distal end of a core wire. The hypotube in turn is connected to a distal atraumatic head. An optical fiber extending along the length of the core wire resides inside the hypotube, proximal but adjacent to the atraumatic head. The optical fiber contains at least three fiber cores, each having a strain-sensing fiber Bragg grating (FBG) with a Bragg wavelength. A collet disposed adjacent to the atraumatic head resides between an annular spring of the hypotube and the strain-sensing FBGs. A light source optically connected to the optical fiber emits light into each of the three fiber cores and their strain-sensing FBGs. Importantly, the emitted light spectrums are broad enough to cover all possible reflection spectrum of the FBGs due to strain and temperature variations imparted to them. Light wavelength detectors are optically connected to the fiber cores, and a controller is operatively coupled to the light wavelength detectors. One of the fiber cores also has a temperature-sensing FBG that is used to compensate for temperature but not strain variations in the strain-sensing FBGs.

In use, the light source emits: light of a first spectrum into the first fiber core and its strain-sensing FBG, light of a second spectrum into the second fiber core and its strain-sensing FBG, light of a third spectrum into the third fiber core and its strain-sensing FBG, and light of a fourth spectrum into the third fiber core and its temperature-sensing FBG. Alternately, there is a dedicated light source for each FBG.

The FBGs reflect light of a Bragg wavelength in a first state when no axial or lateral forces are imparted to the atraumatic head. However, in the case where there is an axial force but no lateral force, the atraumatic head assumes an unarticulated orientation, axially aligned with the guidewire body. In this unarticulated orientation, the atraumatic head does not impinge on the collet so that the collet applies equal radial pressure to each of the strain-sensing FBGs. The respective reflected Bragg wavelengths received by their wavelength detectors are in a second state, shifted a similar or like amount with respect to the first state. A controller optically connected to the optical fiber then calculates the magnitude of the axial force vector imparted to the atraumatic head of the guidewire. The controller is also programmed to use the Bragg wavelength from the temperature-sensing FBG to adjust the axial force vector for the local or ambient temperature inside the vasculature.

When a force having both axial and lateral vectors causes the atraumatic head to deflect out of axial alignment with the guidewire body, the spring of the hypotube is also deflected, which causes the atraumatic head to impinge on the collet. This causes the collet to apply different lateral forces to each of the strain-sensing FBGs. In comparison to when the strain-sensing FBGs reflect light having Bragg wavelengths that are in the first state without axial or lateral forces being imparted to the atraumatic head or in the second state with only an axial force, but no lateral force applied to the atraumatic head, the three reflected Bragg wavelengths from the strain-sensing FBGs are in respective lateral force induced states. The lateral force induced states of the strain-sensing FBGs are converted by the controller into information related to the axial and lateral force vectors imparted to the atraumatic head. The axial and lateral force vectors in turn relate to the pressure being exerted by the atraumatic head against the vasculature tissue and the hardness of the tissue encountered by the guidewire. Thus, the controller is programmed to calculate both axial and lateral forces imparted to the atraumatic head of the guidewire.

In addition to determining the amount of force that the atraumatic head is exerting against body tissue, the controller is programmed to use the axial and lateral force induced states of the FBGs to determine an exact orientational value in an x, y, z coordinate system of the atraumatic head out of axial alignment with the guidewire body.

After the temperature-compensated orientation of the guidewire and its atraumatic head in the vasculature is ascertained, the optical connector enables the proximal and distal optical fibers to be disconnected from each other. Then, a diagnostic or therapeutic instrument, for example a catheter, can be moved along the guidewire to the point of interest in the vasculature of the patient. If the guidewire is left in the vasculature during the medical procedure, the optical connector enables the guidewire and its distal optical fiber to be optically re-connected to the proximal optical fiber. This is useful for letting the surgeon continue to monitor the orientation of the guidewire during the medical procedure. Also, the guidewire needs to be able to be inserted at any rotational angle without significant power loss between the distal and proximal optical fibers across the optical connector.

These and other aspects of the present invention will become increasingly more apparent to those skilled in the art by reference to the following detailed description and to the appended drawings.

BRIEF DESCRIPTION OF THE DRAWINGS

FIG. 2A is an enlarged, partial cross-sectional view of the distal portion of the guidewire 12 shown in FIG. 2.

FIG. 2B is an enlarged view of the indicated region in FIG. 2A showing the optical fiber 14 supporting fiber cores 22, 24 and 26 and their respective strain-sensing FBGs 72, 74 and 76 and the temperature-sensing FBG 75.

FIG. 3 is an exploded, partial cross-sectional view of the distal portion of the guidewire 12 shown in FIG. 2A.

FIG. 4 is a cross-sectional view of the distal portion of the guidewire 12 shown in FIGS. 2 and 2A with the optical fiber 14 residing in a groove 70 in the core wire 48.

FIG. 4A is a cross-sectional view taken along line 4A-4A of FIG. 4.

DETAILED DESCRIPTION OF THE PREFERRED EMBODIMENTS

As used herein, the term "strain-sensing FBG" refers to a fiber Bragg grating whose Bragg wavelength is shifted from a first or baseline wavelength without any strain being imparted to the FBG in an ambient environment to a second Bragg wavelength that is shifted from the first Bragg wavelength in response to at least one of a strain or temperature change having been imparted to the FBG. In other words, the Bragg wavelength of an FBG will shift in response to a change in strain or a change in temperature, or both. In comparison, a "temperature-sensing FBG" is a FBG whose Bragg wavelength will shift in response to a change in strain or a change in temperature, or both, but which is positioned in the guidewire assembly of the present invention so that only temperature changes act on the FBG, but not strain.

Figure 1:
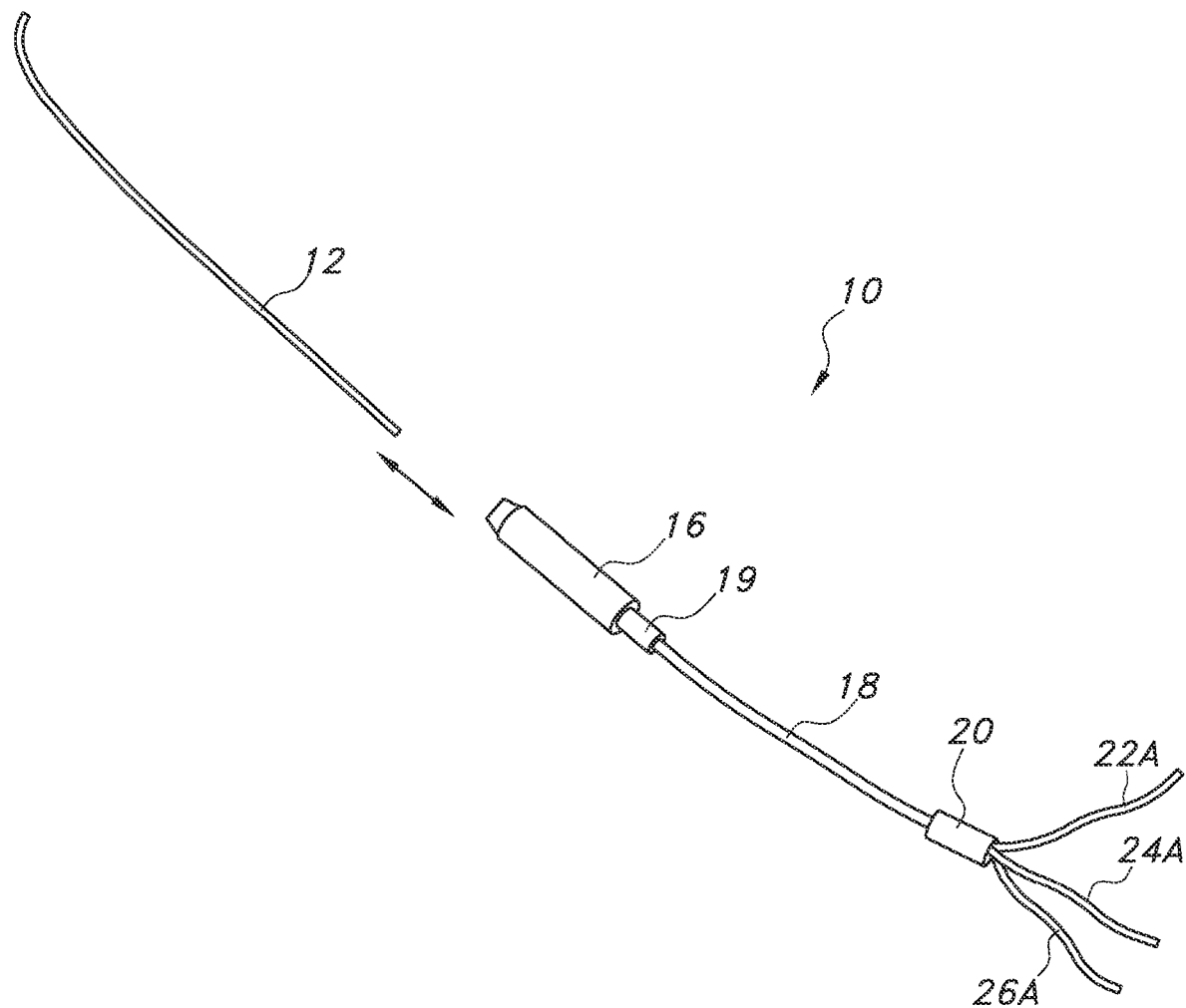
FIG. 1 is a schematic view of a guidewire system 10 according to the present invention.
Figures 2, 2C:
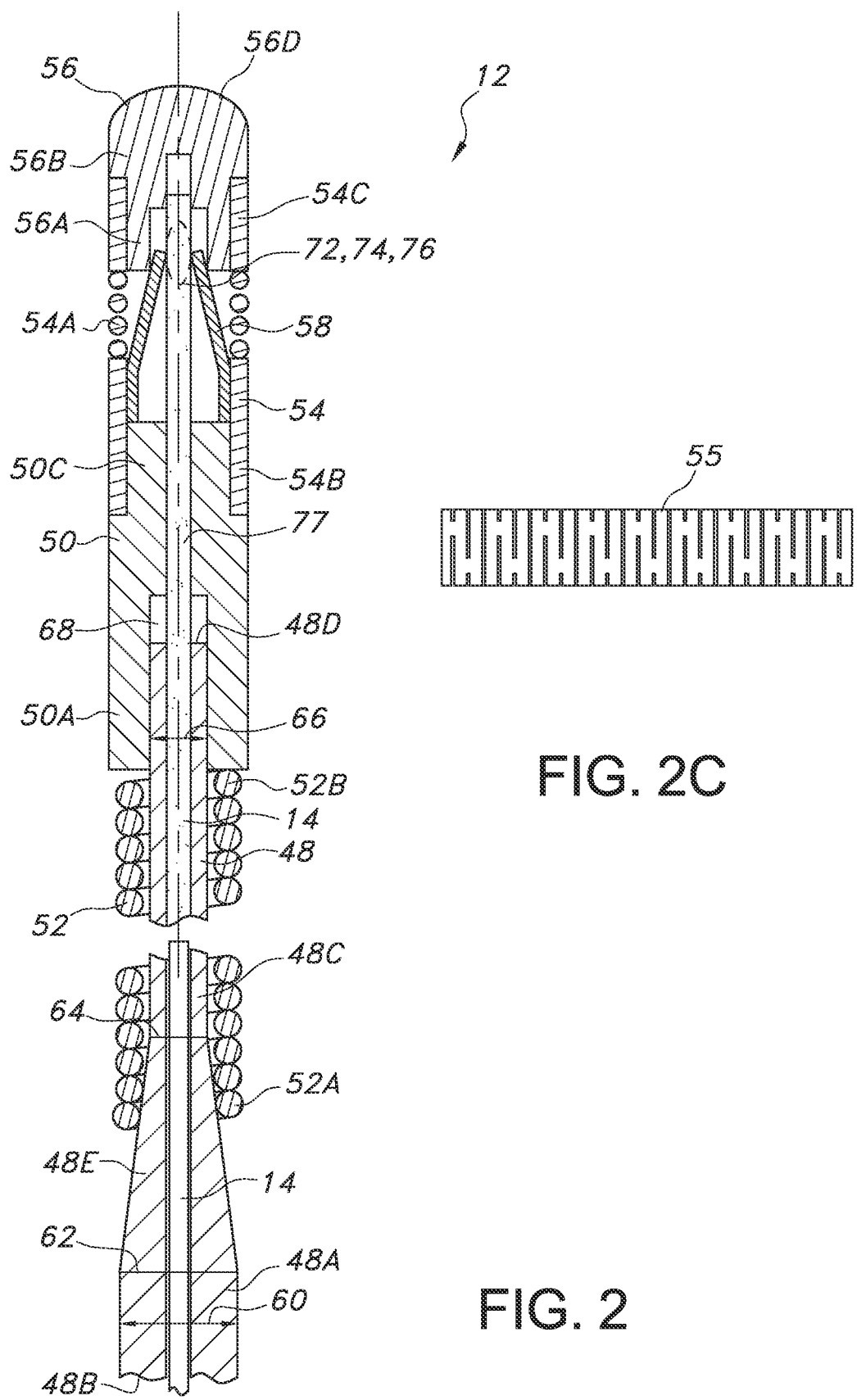
FIG. 2 is a partial cross-sectional view of the guidewire 12 shown in FIG. 1 including a core wire 48 supporting an optical fiber 14 provided with three stain-sensing fiber Bragg gratings (FBGs) 72, 74 and 76 and a temperature-sensing FBG 7?.
FIG. 2C shows that the spring of the distal hypotube 54/spring 54A subassembly shown in FIG. 2 is a slotted spring 55.

Turning now to the drawings, FIG. 1 is a schematic of a guidewire system 10 according to the present invention. The guidewire system 10 comprises a guidewire 12 supporting an optical fiber 14 (FIGS. 2, 2A and 2B). The guidewire and optical fiber are detachably connectable to an optical connector 16. An external optical cable 18 is connected to the optical connector 16 opposite the guidewire 12.

As will be described in detail hereinafter, the optical fiber 14 supported by the guidewire 12 has three fiber cores 22, 24 and 26 (FIG. 2B). The external optical cable 18 has an external optical fiber 18A (FIGS. 6 and 7) comprising three external fiber cores 22A, 24A and 26A (FIGS. 1 and 8) that are optically connected to the respective fiber cores 22, 24 and 26 of the guidewire optical fiber 14 through the optical connector 16. A proximal end of the optical cable 18 connects to a manifold 20 where the fiber cores 22A, 24A and 26A of the external optical fiber 18A fan out for connection to respective circulators 28, 30 and 32 which, in turn, are optically connected to respective broadband light sources 34, 36, 38 and 39, and wavelength detectors 40, 42, 44 and 45, all connected to a controller 46 (FIG. 8).

FIG. 2 is a partial cross-sectional view of an exemplary embodiment of the guidewire 12 shown in FIG. 1. The guidewire 12 extends along a longitudinal axis A-A and is comprised of a core wire 48 supporting an intermediate hypotube 50 residing between a proximal coil spring 52 and a distal hypotube 54/spring 54A subassembly. An atraumatic head 56 is connected to the distal hypotube 54/spring 54A subassembly. The optical fiber 14 having the fiber cores 22, 24 and 26 extends along the core wire 48, the intermediate hypotube 50 and the distal hypotube 54/spring 54A subassembly to the atraumatic head 56. A collet 58 is disposed between the distal spring 54A and the fiber cores 22, 24 and 26. The guidewire 12 has a length ranging from about 50 cm to about 350 cm.

As particularly shown in FIG. 2, the core wire 48 extends from a cylindrically-shaped core wire proximal portion 48A having a proximal end 48B to a cylindrically-shaped core wire distal portion 48C having a distal end 48D. In this exemplary embodiment, the core wire 48 has a substantially constant first outer diameter 60 extending from the core wire proximal end 48B to a first transition indicated at 62. An exemplary first outer diameter ranges from about 0.004 inches to about 0.030 inches. A tapered portion 48E extends distally and downwardly towards the longitudinal axis A-A from the first transition 62 to a second transition indicated at 64 where the core wire distal portion 48C begins. The cylindrically-shaped distal portion 48C has a substantially constant second outer diameter 66, which is less than the first outer diameter 60. An exemplary second outer diameter is about 0.0075 inches. The distal portion 48C extends distally to the distal end 48D of the core wire. If desired, the core wire 48 can be provided with more than one tapered portion. For example, there can be two or more tapered portions, each residing between proximal and distal cylindrically-shaped core wire portions. The core wire 48 is preferably made of stainless steel or nitinol. Nitinol is a superelastic nickel-titanium alloy wire comprising, for example, a composition in the range of from about 54 atomic % nickel: about 46 atomic % titanium to about 57 atomic % nickel: about 43 atomic % titanium.

The proximal coil spring 52 is made of stainless steel, preferably 304 stainless steel, and has a proximal end 52A connected to the tapered portion 48E of the core wire 48. The opposite distal end 52B of the proximal coil spring terminates at a position that is proximal the core wire distal end 48D. That way, the core wire distal portion 48C extends distally and outwardly beyond a distal end of the proximal coil spring 52. The connections between the proximal end of the proximal coil spring 52A and the tapered portion 48E of the core wire and between the distal end 52B of the proximal coil spring and the core wire distal portion 48C are individually made as a laser welder, a braze, or using a solder, and the like.

FIGS. 2, 2A and 3 show that the intermediate hypotube 50 supported on the cylindrically-shaped distal portion 48C of the core wire 48 has a cylindrically-shaped proximal portion 50A that extends distally to an outer annular step 50B meeting a cylindrically-shaped distal portion 50C. A proximal lumen 50D extends from a proximal end of the hypotube part-way along the length of the proximal portion 50A. The proximal lumen 50D of the hypotube meets a distal lumen 50E at an inner annular step 50F with the distal lumen 50E extending the rest of the length of the hypotube to a distal end thereof.

The distal portion 48C of the core wire 48 is received in the proximal lumen 50D of the hypotube 50, however, a gap 68 resides between the distal end 48D of the core wire and the inner step 50F. The gap 68 allows the optical fiber 14 to bend from the axially centered lumen of the hypotube 50 toward the outer surface of the core wire 48. Suitable materials for the intermediate hypotube 50 include stainless steel, nickel, titanium, platinum, platinum iridium, and a medical grade durable plastic.

The distal hypotube 54/spring 54A subassembly is a cylindrically-shaped member having the coil spring 54A residing between a proximal sleeve-shaped portion 54B and a distal sleeve-shaped portion 54C. Alternately, FIG. 2C shows that the spring of the distal hypotube 54/spring 54A subassembly is a slotted spring 55 residing between the proximal and distal sleeve-shaped portions 54B, 54C. Whether it is a coil spring 54A or a slotted spring 55, the distal spring is preferably made of stainless steel or nitinol.

The distal cylindrically-shaped portion 50C of the intermediate hypotube 50 is received inside the proximal sleeve 54B of the distal hypotube 54/spring 54A subassembly. In that manner, the outer surface of the intermediate hypotube 50 is substantially coaxially aligned with the outer surface of the distal hypotube 54/spring 54A subassembly.

In an alternate embodiment, intermediate hypotube 50 and the distal hypotube 54/spring 54A subassembly are a unitary or single member.

The atraumatic head 56 has a cylindrically-shaped proximal head portion 56A that extends to a distal head portion 56B of a greater diameter than the proximal head portion. The proximal and distal head portions 56A, 56B meet at an outer annular step 56C (FIG. 3). In turn, the cylindrically-shaped distal head portion 56B extends to a dome-shaped atraumatic surface 56D that is polished smooth to help minimize tissue damage and trauma as the guidewire 12 is moved through a vasculature. With the proximal portion 56A of the atraumatic head 56 received inside the lumen formed by the distal sleeve 54C of the distal hypotube 54/spring 54A subassembly, the cylindrically-shaped outer surface of the distal spring 54A is substantially coaxially aligned with the cylindrically-shaped outer surface of the distal portion 56B of the atraumatic head 56. Suitable materials for the atraumatic head 56 include stainless steel, nickel, titanium, platinum, and platinum/iridium.

The atraumatic head 56 is further provided with a proximal channel 56E that is aligned along the longitudinal axis A-A of the guidewire. The proximal channel 56E meets a lesser diameter distal channel 56F at an inner annular step 56G. The distal channel 56F resides partly in the cylindrically-shaped proximal portion 56A of the atraumatic head 56 and partly in the distal portion thereof, terminating proximal the atraumatic surface 56D.

FIG. 4 shows the optical fiber 24 residing in a groove 70 extending along the proximal portion 48A, the tapered portion 48E and the distal portion 48C of the core wire. If the groove 70 is large enough, the gap 68 discussed above may not be needed. Instead, the groove 70 provides enough room for the optical fiber 14 to move out of axial alignment as the guidewire 12 bend through a vasculature.

As further shown in FIGS. 2, 2A and 3, the optical fiber 14 continues distally through the lumen formed by the proximal coil spring 52 and into the proximal and distal lumens 50D and 50E of the intermediate hypotube 50, through the distal hypotube 54/spring 54A subassembly and into the atraumatic head 56. There, the optical fiber 14 at least partially resides in the distal channel 56F adjacent to the inner annular step 56G of the atraumatic head 56. In that manner, the distal channel 56F provides a gap so that the atraumatic tip 56 can slide up and down over the optical fiber 14.

As shown in FIG. 2B, the optical fiber 14 is provided with three fiber cores 22, 24 and 26 that are evenly spaced at 120° annular intervals about the longitudinal axis A-A and with respect to each other inside the optical fiber. The fiber cores 22, 24 and 26 contain respective strain-sensing fiber Bragg gratings (FBG) 72, 74 and 76. Fiber core 26 additionally contains a temperature-sensing FBG 77. The FBGs are individually selected from a phase-shifted FBG, a long-period FBG, an apodized FBG, a chirped FBGs and a tilted FBG.

As shown in FIGS. 2, 2A and 3, the collet 58 has a cylindrically-shaped proximal portion 58A that is received in the inner diameter of the proximal sleeve 54B of the distal hypotube 54/spring 54A subassembly, abutting a distal face of the intermediate hypotube 50. The collet 58 has tapered cam fingers 58B that extends distally and downwardly toward the longitudinal axis A-A of the guidewire 12. The collet cam fingers 58B reside inside the distal spring 54A and inside the proximal portion 56A of the atraumatic head 56 and are radially aligned with the strain-sensing FBGs 72, 74 and 76 of the fiber cores 22, 24 and 26 of the optical fiber 14. With the guidewire 12 in a neutral orientation aligned along the A-A axis, proximal portion 56A of the atraumatic head 56 rests against the collet cam fingers 58B and the collet cam fingers 58B rest against an outer surface of the optical fiber 14, not imparting any strain on the FBGs 72, 74 and 76. Suitable materials for the collet 58 include stainless steel, nickel titanium, platinum, platinum iridium, and a medical grade durable plastic.

Figure 5:
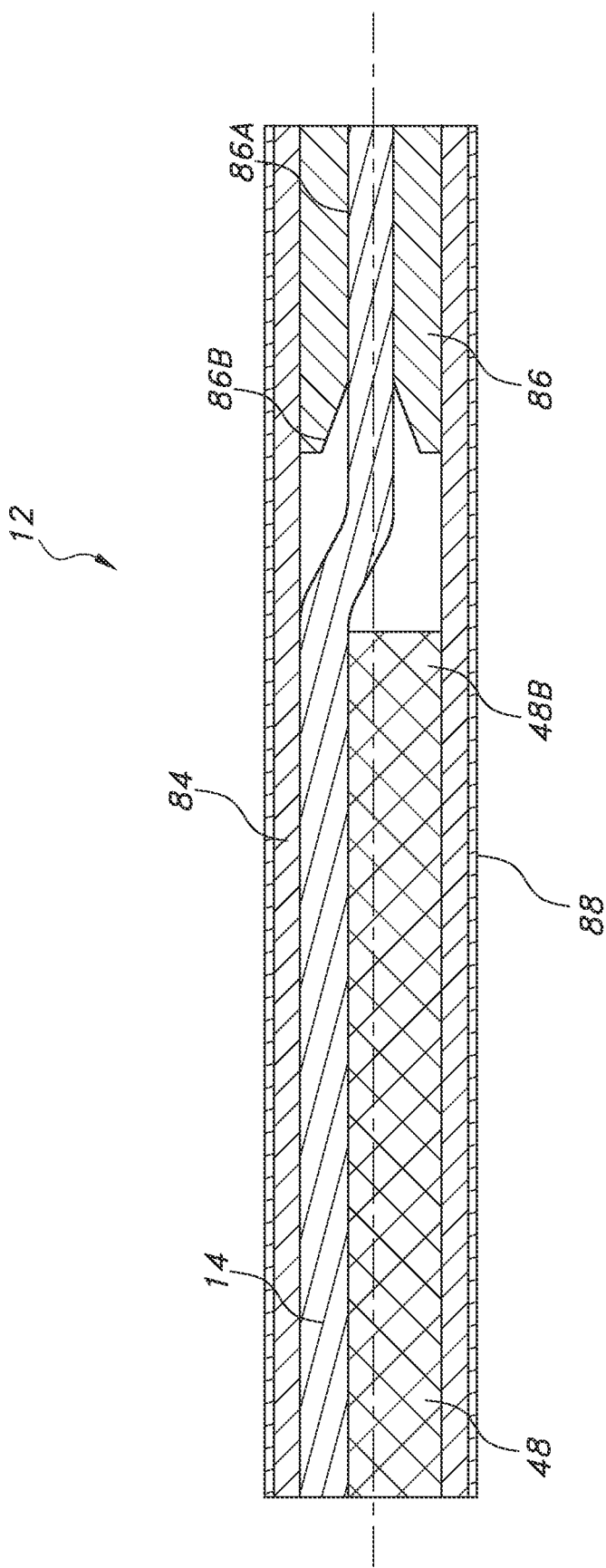
FIG. 5 is a cross-sectional view of the proximal end of the guidewire 12 shown in FIGS. 2, 4 and 4A with the optical fiber 14 supported in a groove 70 of the core wire 48 and having its proximal end connected to a proximal ferrule 86 residing in a proximal hypotube 84.

FIG. 5 shows the proximal end of the guidewire 12 supporting the optical fiber 14. The proximal end 48B of the core wire 48 resides inside and is connected to a cylindrically-shaped proximal hypotube 84. A ferrule 86 is also supported inside the hypotube 84, spaced proximally from the proximal end 48B of the core wire 48. The ferrule 86 is a cylindrically-shaped member having at lumen 86A extending to a taper 86B. The optical fiber 14 residing in the groove 70 in the core wire 48 shown in FIGS. 4 and 4A resides in this lumen 86A. The ferrule taper 86B aids in making this connection.

Preferably, a lubricious coating 88 is provided on the core wire 48 and hypotube 84. The lubricious coating 88 helps to reduce friction between the guidewire 12 and body tissue as the guidewire is moved through a vasculature. Suitable coatings for this purpose are described in U.S. Pat. No. 9,255,173 to Edwards, U.S. Pat. No. 9,623,157 to Edwards and U.S. Pat. No. 9,714,361 to Edwards, and in U.S. Pub. Nos. 2014/0275340 to Edwards, 2016/0160078 to Edwards and 2020/0131399 to Edwards, all of which are assigned to the assignee of the present invention and incorporated herein by reference. Suitable lubricious coatings are also described in U.S. Pat. No. 7,776,956 to Webster at al. and U.S. Pat. No. 9,676,895 to Harkal et al.

Figure 6:
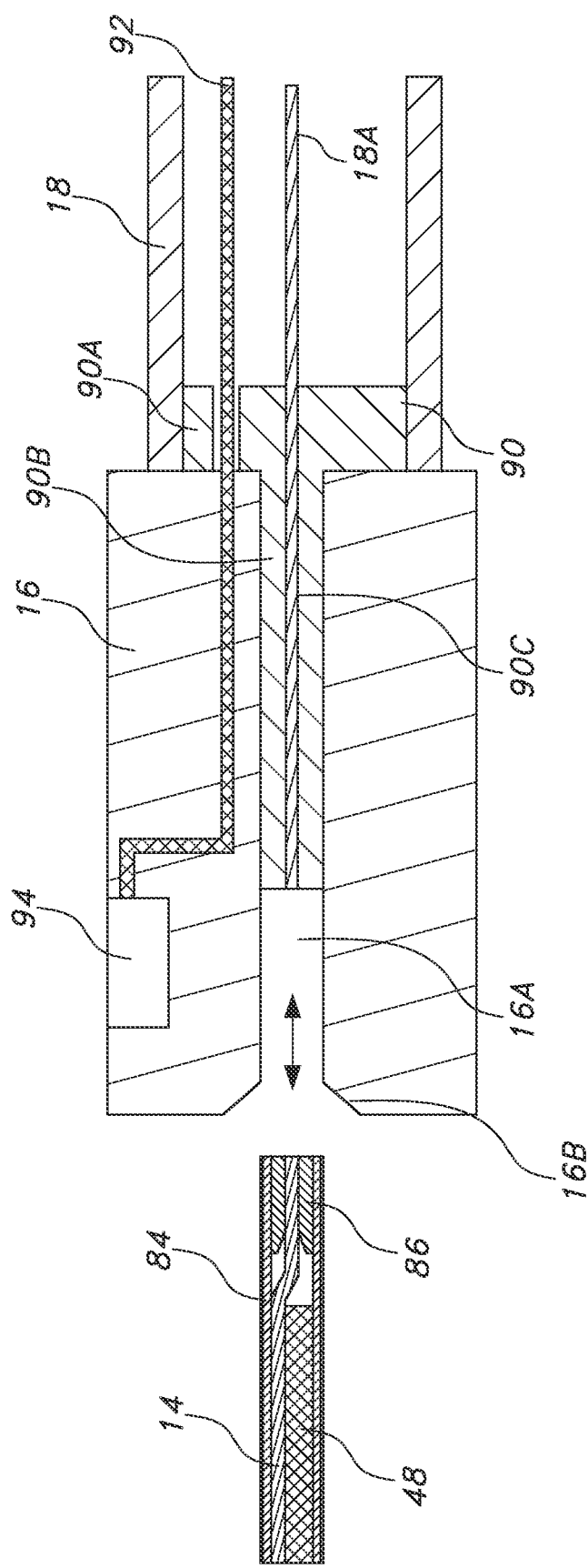
FIG. 6 is a schematic view of the guidewire 12 shown in FIGS. 1 and 5 being moved into the optical connector 16 of the guidewire system 10.

FIG. 6 illustrates the guidewire 12 being moved into the optical connector 16 shown in FIG. 1. The optical connector 16 has a lumen 16A extending to a distal taper 16B. An insert 90 has an enlarged head 90A connected to a proximal ferrule 90B. A lumen 90C extends through the enlarged head 90A and ferrule 90B of the connector insert 90. The distal end of the optical fiber 18A of the external optical cable 18 resides in the proximal ferrule 90B of the insert 90 with the proximal ferrule 90B in turn residing in the connector lumen 16A. A strain-relief sleeve 19 (FIGS. 1 and 8) adds support to the optical cable 18 and helps prevent wear and chafing of the cable against the optical connector 16.

Figure 7:
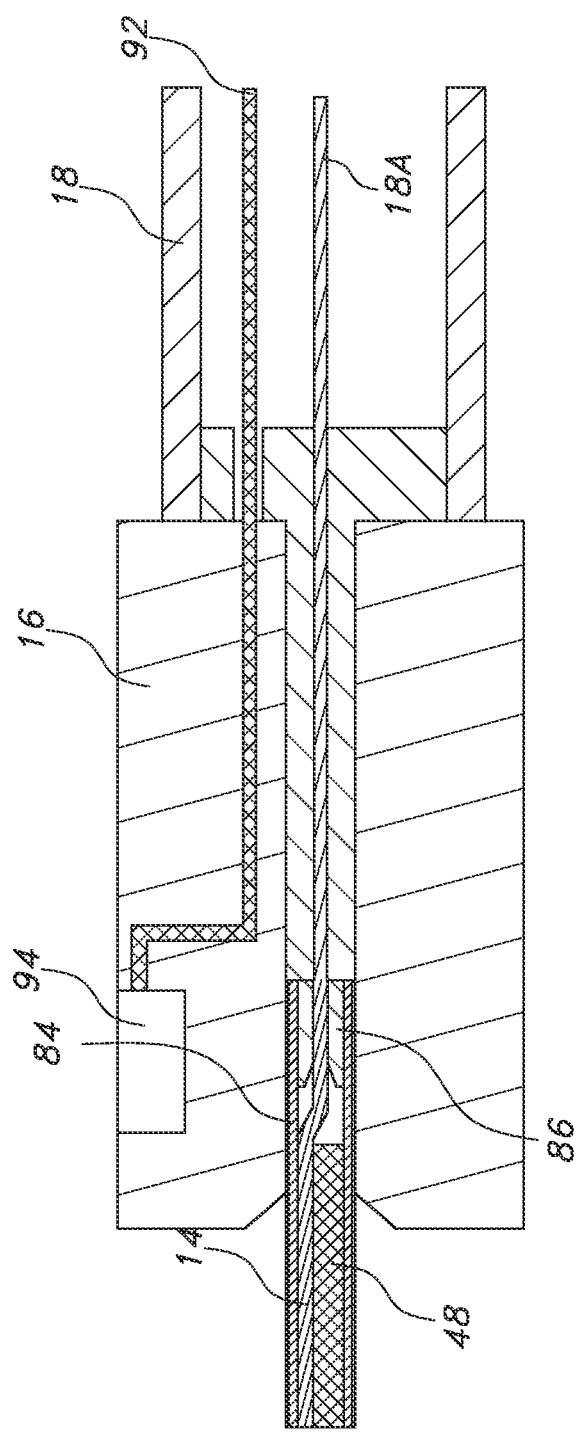
FIG. 7 is a schematic view of the guidewire 12 shown in FIGS. 1 and 5 with the optical fiber 14 now being optically connected to an external optical cable 18 in the optical connector 16.
Figure 8:
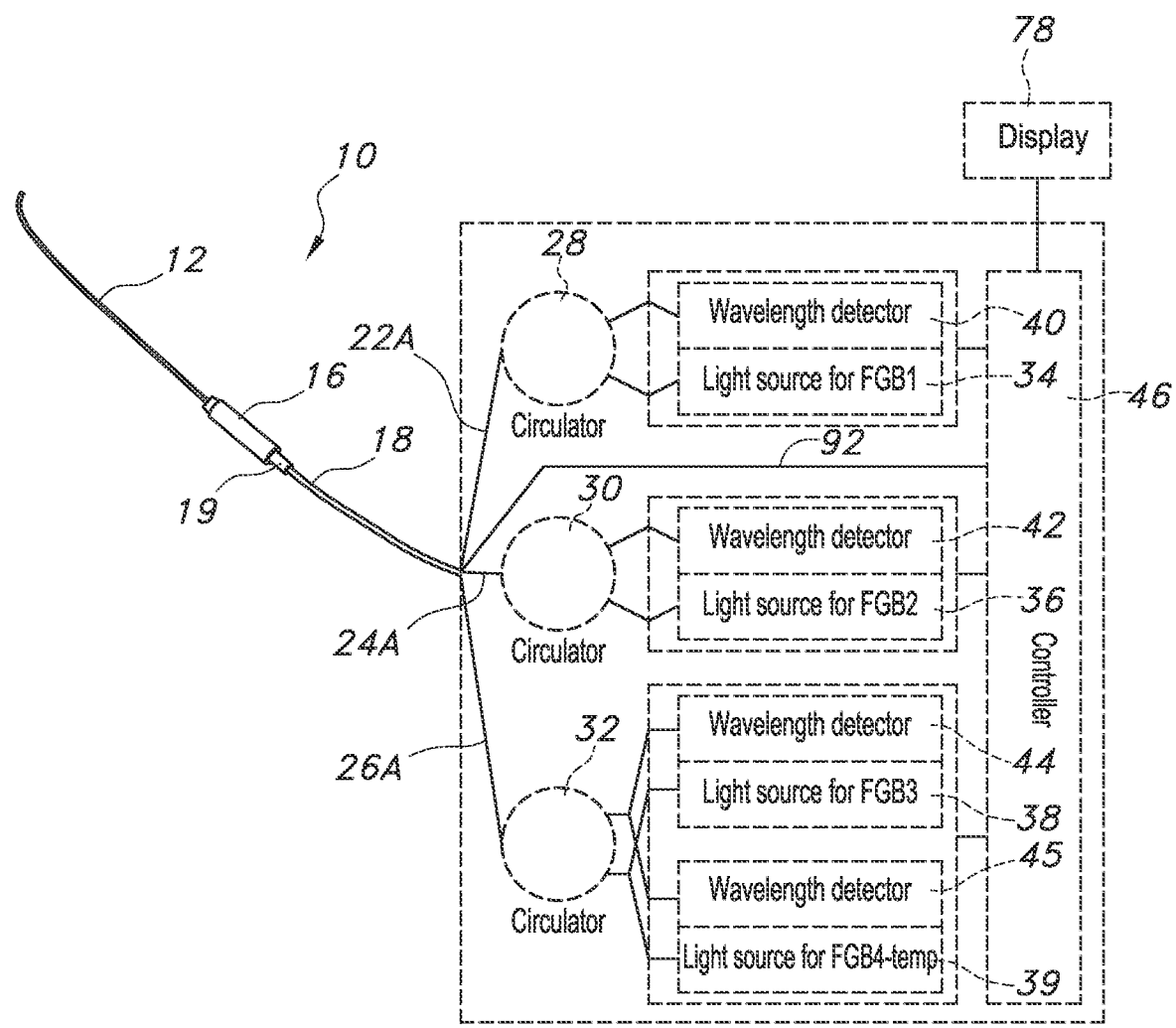
FIG. 8 is a schematic of the guidewire system 10 shown in FIG. 1 including the optical fiber 14 supporting fiber cores 22, 24 and 26 and their respective strain-sensing FBGs 72, 74 and 76 and the temperature-sensing FBG 77 shown in FIGS. 2, 2A and 2B being optically connected to respective light sources 34, 36, 38 and 39 and wavelength detectors 40, 42, 44 and 45.

FIG. 7 shows the optical fiber 14 of the guidewire 12 optically connected to the external optical cable 18 in the connector 16. In the optical connector 26, the fiber cores 22, 24 and 26 of the guidewire optical fiber 14 are optically connected to respective external fiber cores 22A, 24A and 26A comprising the optical fiber 18A of the external optical cable 18.

As schematically shown in FIG. 8, the external fiber cores 22A, 24A and 26A are optically connected to dedicated broadband light sources 34, 36, 38 and 39. More specifically, fiber core 22A is optically connected to a first broadband light source 34, fiber core 24A is optically connected to a second broadband light source 36, and fiber core 26A is optically connected to a third broadband light source 38 and to a fourth light source 39. In another embodiment, there is only one broadband light source that selectively emits light into each external fiber core 22A, 24A and 26A.

The first light source 60A emits light of a first spectrum through a first circulator 28 into the external fiber core 22A optically connected to the fiber core 22 of the optical fiber 14 in the guidewire 12 and its associated strain-sensing FBG 72. The first light spectrum covers all possible reflection spectrum from the strain-sensing FBG due to strain and temperature variations imparted to the FBG 72. Similarly, the second light source 36 emits light of a second spectrum through a second circulator 30 into the external fiber core 24A optically connected to the fiber core 24 of the optical fiber 14 and its associated strain-sensing FBG 74. The second light spectrum covers all possible reflection spectrum from the strain-sensing FBG due to strain and temperature variations imparted to the FBG 74. Further, the third light source 38 emits light of a third spectrum through a third circulator 32 into the external fiber core 26A optically connected to the fiber core 26 of the optical fiber 14 and its associated strain-sensing FBG 76. The third light spectrum covers all possible reflection spectrum from the strain-sensing FBG due to strain and temperature variations imparted to the FBG 76.

And, the fourth light source 39 emits light of a fourth spectrum through the third circulator 32 into the external fiber core 26A optically connected to the fiber core 26 of the optical fiber 14 and its associated temperature-sensing FBG 77. The fourth light spectrum covers all possible reflection spectrum from the temperature-sensing FBG due to strain and temperature variations imparted to the FBG 77. However, since FBG 77 resides in the lumen 50E of the hypotube 50, the Bragg wavelength of this FBG is only affected by temperature. Ever though FBG 77 is susceptible to strain, lumen 50E protects the FBG 77 from strain.

A fiber Bragg grating (FBG) is a periodic modulation of the refractive index along the respective fiber cores 22, 24 and 26 of the optical fiber 14. The periodicity results in reflection of light waves that match the periodic spacing of the FBG wavelength while other wavelengths are transmitted unperturbed. A FBG in a single mode fiber core will reflect light waves of a wavelength centered around a single wavelength (a Bragg wavelength) as determined by the effective refractive index and the period of the grating. In that manner, the wavelength that is reflected by the FBG is determined by the "effective refractive index" of the grating in the fiber core and the period of the grating. By altering these elements (the effective refractive index and the period of the grating), it is possible to configure the optical fiber 14 containing the fiber cores 22, 24 and 26 and their respective strain-sensing FBGs 72, 74 and 76 and the temperature-sensing FBG 77 to reflect light around two, three or more different wavelengths.

Figure 9A:
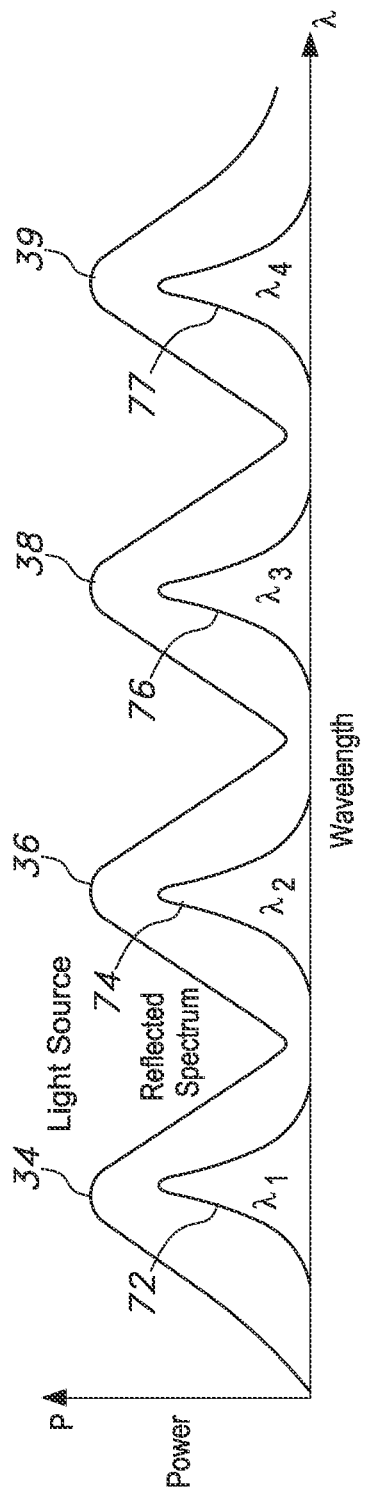
FIG. 9A is a graph depicting the dedicated light sources 34, 36 and 38, each emitting light at a spectrum that covers all possible reflection spectrum from the respective strain-sensing FBGs 72, 74 and 76 and the temperature-sensing FBG 77 due to strain and temperature variations imparted to the FBGs.

As depicted in FIG. 9A, in a four-FBG system with dedicated light sources 34, 36, 38 and 39, the light sources each emit light at a spectrum that covers all possible reflection spectrum from the respective strain-sensing FBGs 72, 74 and 76 due to strain and temperature variations imparted to the FBGs and the temperature-sensing FBG due to temperature variations imparted to the FBG 77. Preferably, the strain-sensing FBGs 72, 74 and 76 and the temperature-sensing FBG 77 reflect light of different Bragg wavelengths having respective peaks at $\lambda_1$, $\lambda_2$, $\lambda_3$ and $\lambda_4$. A narrow linewidth laser is suitable for the dedicated light sources 34, 36, 38 and 39.

Figure 9B:
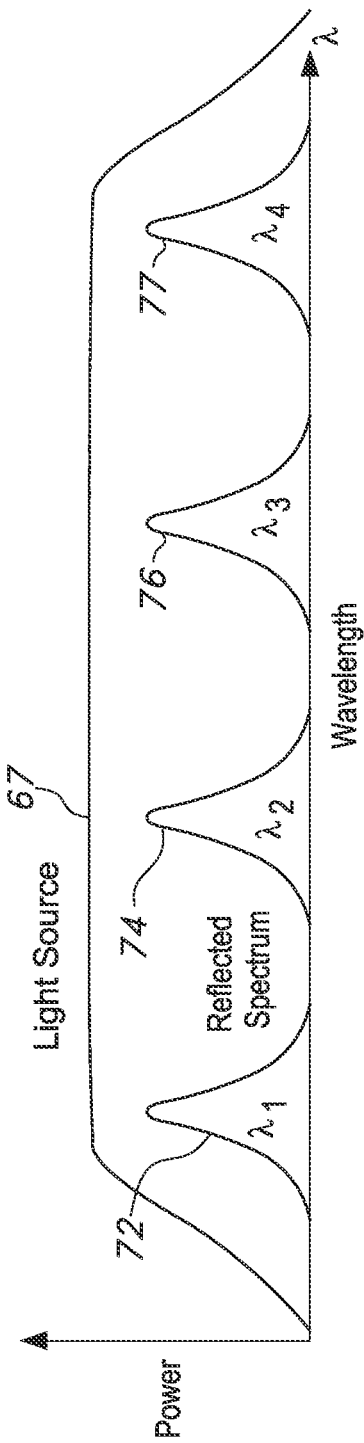
FIG. 9B is a graph depicting a three-fiber core system using one broadband light sources 67 that emits light at a spectrum that covers all possible reflection spectrum from the strain-sensing FBGs 72, 74 and 76 and the temperature-sensing FBG 77 due to strain and temperature variations imparted to the FBGs.

FIG. 9B depicts a four-FBG system using one broadband light source 67 that emits light at a spectrum covering all possible reflection spectrum from the respective strain-sensing FBGs 72, 74 and 76 due to strain and temperature variations imparted to the FBGs and the temperature-sensing FBG due to temperature variations imparted to the FBG 77. As with the embodiment shown in FIG. 9A, the strain-sensing FBGs 72, 74 and 76 and the temperature-sensing FBG 77 reflect light of different Bragg wavelengths having respective peaks at $\lambda_1$, $\lambda_2$, $\lambda_3$ and $\lambda_4$. A Superluminescent Light Emitting Diode (SLED) or a scanning laser is a suitable broadband light source.

In either the dedicated light source embodiment (FIG. 9A) or the broadband light source embodiment (FIG. 9B), light reflected by the FBGs 72, 74, 76 and 77 returns via their respective circulator 28, 30 and 32 into a corresponding wavelength detector 40, 42, 44 and 45. Each detector analyzes the light it receives to identify the intensity of the light at various wavelengths. This information is forwarded to the controller 46 where the intensity of the reflected light is used to calculate the magnitude of the axial and lateral forces applied to the atraumatic head 56 of the guidewire 12 and the temperature of the local environment.

With the strain-sensing FBGs 72, 74 and 76 being in a first or neutral state without any axial force imparted to the atraumatic head 56, the collet cam fingers 58B of the distal hypotube 54/spring 54A subassembly do not apply any lateral force to the strain-sensing FBGs 72, 74 and 76. In this first state, there is no shift in the reflected light and the reflected light spectrum will be that as presented in either FIG. 9A or 9B depending on the type of light source. The controller 46 is programmed to calculate that no lateral force is applied to the strain-sensing FBGs 72, 74 and 76.

In a second state with only an axial force but no lateral force applied to the atraumatic head 56, the proximal portion 56A of the atraumatic head 56 applies an equal lateral force to the collet cam fingers 58B of the distal hypotube 54/spring 54A subassembly and the collet cam fingers 58B in turn apply an equal lateral force to each of the strain-sensing FBGs 72, 74 and 76. In this second state, there is a shift in the reflected light and the reflected light spectrum presented in either FIG. 9A or FIG. 9B has each of the wavelength peaks $\lambda_1$, $\lambda_2$ and $\lambda_3$ shifted a similar or like amount. Again, the controller 46 is programmed to use the shift in the wavelength peaks $\lambda_1$, $\lambda_2$ and $\lambda_3$, to calculate the magnitude of the axial force applied to the strain-sensing FBGs 72, 74 and 76. Further, the controller 46 is programmed to use the shift in the wavelength peak $\lambda_4$ to compensate the strain-sensing wavelength peaks $\lambda_1$, $\lambda_2$ and $\lambda_3$ for the local or ambient temperature.

Any shift or movement in the wavelength peaks of the strain-sensing FBGs 72, 74 and 76 with respect to those peaks in the first state without an axial force being imparted to the atraumatic head 56 or with respect to those peaks in the second state with only an axial force but no lateral force being imparted to the atraumatic head is indicative of strain from the atraumatic head 56 contacting the collet cam fingers 58B and in turn the collet cam fingers 58B contacting the strain-sensing FBGs 72, 74 and 76 with forces of different axial and lateral magnitudes. With the atraumatic head 56 in an orientation out of axial alignment, forces of different axial and lateral magnitudes are directed to the respective strain-sensing FBGs 72, 74 and 76 by the collet cam fingers 58B. Then, relative movement of the wavelength peaks $\lambda_1$, $\lambda_2$ and $\lambda_3$ due to axial and lateral forces or strain directed at each of the strain-sensing FBGs 72, 74 and 76, compensated for by the temperature-sensing FBG 77, is converted by the controller 46 into a value related to the force that the atraumatic head 56 is exerting against body tissue. The controller 46 is also programmed to calculate a spatial orientation in an x, y, z coordinate system of the atraumatic head 56 in the vasculature from the relative movement of the wavelength peaks $\lambda_1$, $\lambda_2$ and $\lambda_3$ due to axial and lateral forces or strain directed at each of the strain-sensing FBGs 72, 74 and 76.

FIG. 8 illustrates that the controller 46 has a visual display 78. As described above, the controller 46 is programmed to calculate the spatial orientation of the atraumatic head 56 in the vasculature and the force that the atraumatic head is exerting against body tissue, for example, against an occlusion. Among other useful information, the display 78 presents this orientation and force information in real-time in any one of a variety of formats that are useful to the surgeon.

As previously described, during movement of the guidewire 12 through the vasculature (both forward and rearward movement), frictional feedback from the surface of the shaft of the guidewire dominates the tactile feel in the surgeon's hand while tactile perception of the force acting at the atraumatic head 56 is minimal. Therefore, there is a risk of vessel injury including perforation due to the force of the guidewire 12 including its atraumatic head 56 against the vasculature tissue.

To overcome this, axial and lateral forces imparted to the atraumatic head 56 are not only fed back to the controller 16 for presentation by the display 78 as described above, but the controller also sends a haptic or tactile feedback signal through an electrical cable 92 to an electromechanical actuator 94 integrated into the connector 16. Haptic or tactile feedback is the use of vibration patterns to convey information to a user or operator. Haptic feedback uses the electromechanical actuator 94 to send haptic feedback signals to the electromechanical actuator 94, which can be felt by the surgeon holding the connector 16. Exemplary electromechanical actuators include a vibration motor, an eccentric rotating mass (ERM) actuator driven by an electronic circuit, a linear resonant actuator, and a piezoelectric actuator.

In the guidewire system of the present invention, an exemplary embodiment has the vibration increase in frequency or amplitude depending on the calculated temperature-compensated force of the atraumatic head 56 against vasculature tissue. Further, the vibrational frequency can be varied to indicate the direction of the force while the amplitude of the vibration can be varied to indicate the magnitude of the axial and lateral force vectors. That way, the surgeon feels the magnitude and direction of the axial and lateral force vectors in his hand as the atraumatic head 56 of the guidewire 12 is moved through the vasculature during a medical procedure.

This haptic or tactile feedback to the surgeon helps reduce the risk of damaging tissue, speeds up the medical procedure and reduces contrast and x-ray use. Also, the haptic or tactile feedback correlates with the hardness of the tissue encountered by the atraumatic head 56. This helps reduce the x-ray requirement further. The force data at the occlusion also conveys information on the make-up of the occlusion, such as how calcified it is, which is an important consideration when making treatment decisions such as whether to insert a stent, or not.

Figure 10:
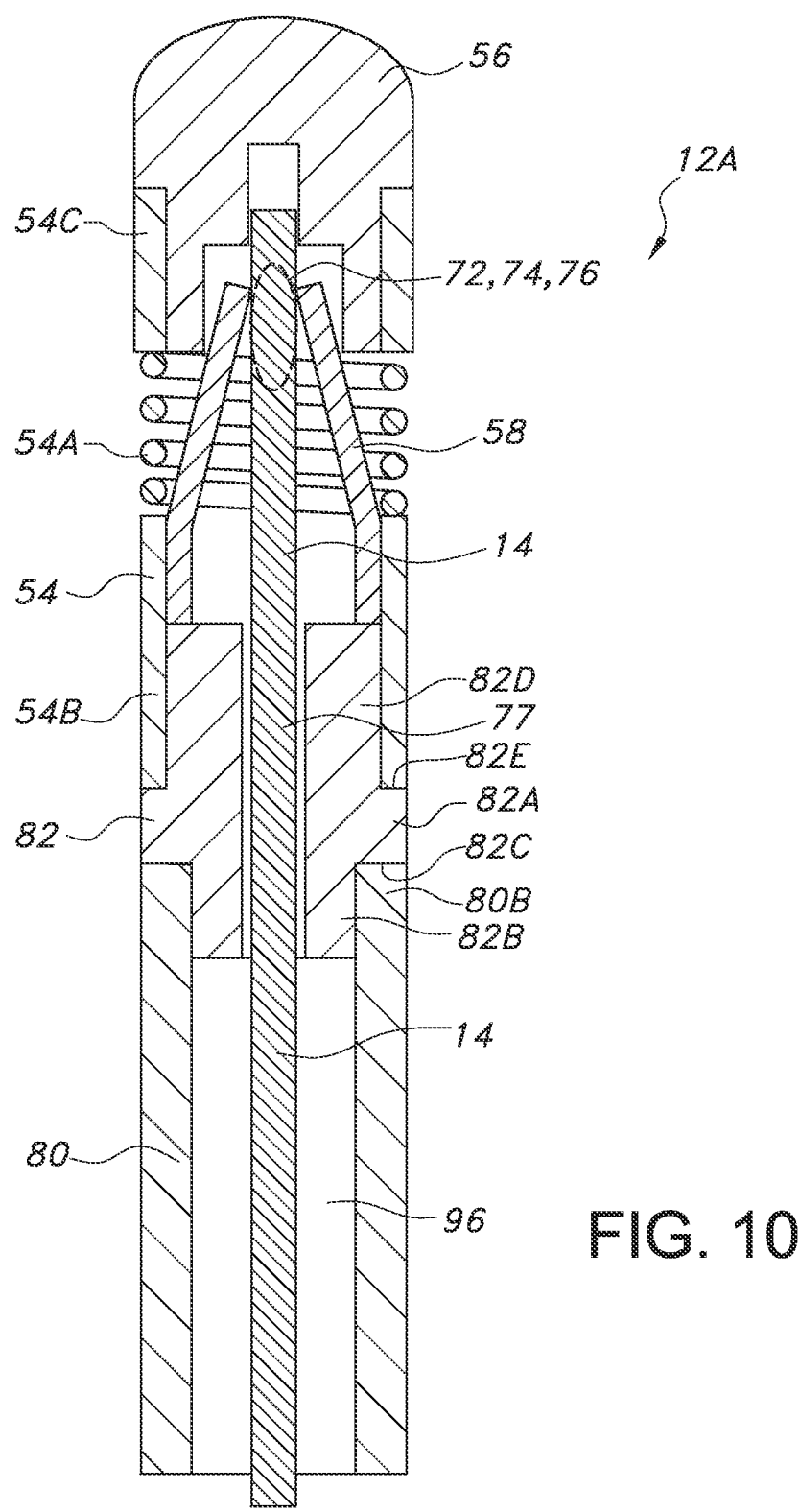
FIG. 10 is a cross-sectional view of another embodiment of a guidewire 12A according to the present invention comprising an optical fiber 14 residing inside a proximal hypotube 80 and supporting core wires having FBGs 72, 74 and 76 where the optical fiber extends to a distal atraumatic tip 56.
Figure 11:
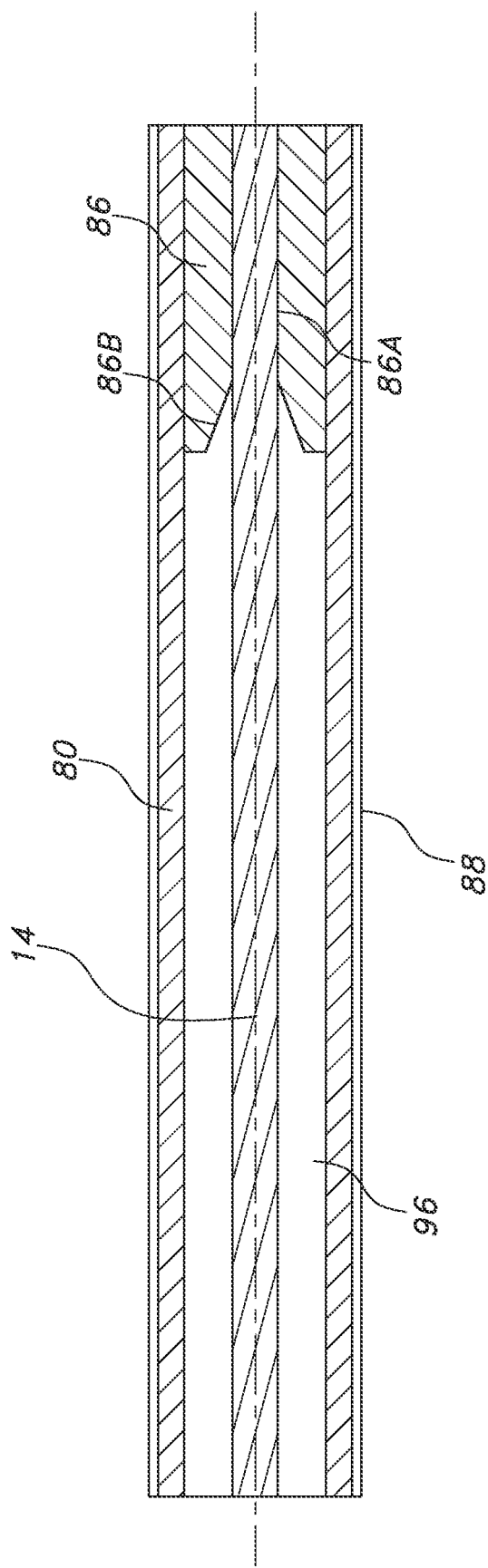
FIG. 11 is a cross-sectional view of the proximal end of the guidewire 12A shown in FIG. 10 with the optical fiber 14 connected to a proximal ferrule 86 residing in the proximal hypotube 80.

FIG. 10 illustrates an alternate embodiment of a guidewire 12A according to the present invention. This guidewire 12A is similar to the guidewire 12 shown in FIGS. 1, 2, 2A, 2B, 2C and 3 to 8 except that the proximal coil spring 52 has been replaced with an elongate proximal hypotube 80, and a connection hypotube 82 that is configured to connect to the proximal hypotube 80, and the distal hypotube 54/spring 54A subassembly has replaced the intermediate hypotube 50. The proximal hypotube 80 is a cylindrically-shaped member extending from a proximal end 80A that is detachably connectable to the proximal optical connector 16 to a distal end 80B.

The connection hypotube 82 has an intermediate cylindrically-shaped portion 82A that meets a proximal cylindrically-shaped portion 82B at a proximal step 82C and a distal cylindrically-shaped portion 82D at a distal step 82E. The proximal cylindrically-shaped portion 82B of the connection hypotube 82 is received in the distal end 80b of the proximal hypotube 80 abutting step 82C. Similarly, the distal cylindrically-shaped portion 82D of the connection hypotube 82 is received in the proximal sleeve 54B of the distal hypotube 54/spring 54A subassembly, abutting step 82E. In this assembly, the outer surface of the proximal hypotube 80, the intermediate cylindrically-shaped portion 82A of the connection hypotube 82, and the distal hypotube 54/spring 54A subassembly are of a similar diameter and aligned with each other. Further, the proximal hypotube 80 has a lumen 96 through which the optical fiber 14 extends. This embodiment of the guidewire 12A of the present invention does not have a core wire.

In Use

With the atraumatic head 56 of guidewire 12 (FIGS. 2, 2A, 4) or of guidewire 12A (FIG. 10) being in a neutral, unarticulated orientation, the proximal portion 56A of the atraumatic head 56 rests against the collet cam fingers 58B of collet 58 and the cam fingers 58B rest against an outer surface of the optical fiber 14, not imparting any strain on the FBGs 72, 74 and 76. With the dedicated light sources 34, 36, 38 and 39 or the broadband light source 67 emitting the first light spectrum into the first strain-sensing FBG 72, the second light spectrum into the second strain-sensing FBG 74, the third light spectrum into the third strain-sensing FBG 76, and the fourth light spectrum into the fourth temperatures-sensing FBG 77, in comparison to a first state of the reflected first, second and third Bragg wavelengths with no axial or lateral forces imparted to the atraumatic head 56, with an axial force but no lateral force imparted to the atraumatic head to cause the atraumatic head to assume a neutral, unarticulated orientation axially aligned with the guidewire body 12 or 12A, the proximal portion 56A of the atraumatic head 56 applies an equal radial pressure to the collet cam fingers 58B and the collet cam fingers 58B apply equal radial pressure to the first, second and third strain-sensing FBGs. The reflected first, second and third strain-related Bragg wavelengths $\lambda_1$, $\lambda_2$ and $\lambda_3$ received by the respective first, second, and third Wavelength detectors 72, 74 and 76 are in a second state, shifted a similar or like amount with respect to the first state.

To begin a medical procedure, the surgeon first makes an incision in the skin to access the vasculature. As the surgeon advances the atraumatic head 56 through the vasculature to the body site of interest, for example, to an occlusion, the axial and lateral forces acting on the atraumatic head 56 are precisely monitored by measuring the reflected Bragg wavelength of the reflected light from each of the strain-sensing FBGs 72, 74 and 76. That is as the atraumatic head 56 flexes or bends at the distal hypotube 54/spring 54A subassembly to assume an articulated orientation (depicted in FIGS. 1 and 8), the proximal portion 56A of the atraumatic head 56 contacts the collet cam finger 58B and the collet cam fingers 58B are moved out of alignment with the aligned axes of the guidewire body 12, 12A and its atraumatic head 56.

As the atraumatic head 56 moves into an articulated orientation, out of axial alignment with the guidewire body 12, 12A, the proximal portion 56A of the atraumatic head 56 applies a lateral force to the collet cam fingers 58B and the collet cam fingers 58B apply a lateral force against one of the strain-sensing FBGs 72, 74 and 76 with a greater magnitude than against the other strain-sensing FBGs. The relative lateral force or strain imparted to each FBG 72, 74 and 76 changes the reflected Bragg wavelength from the strain-sensing FBGs 72, 74 and 76. The altered Bragg wavelength of the reflected light from each FBG 72, 74 and 76 is measured by their respective wavelength detector 40, 42 and 44 and sent to the controller 46 for processing into useful information to the surgeon. The temperature-sensing FBG 77 is used to compensate the altered Bragg wavelength of the reflected light from each FBG 72, 74 and 76 for changes in the local or ambient temperature.

In that respect, when a lateral force is imparted to the atraumatic head to cause the atraumatic head 56 to deflect out of axial alignment with the guidewire body 12, 12A, the spring 54A of the distal hypotube 54/spring 54A subassembly deflects out of axial alignment to cause the proximal portion 56A of the atraumatic head 56 contacts the collet cam finger 58B and the collet cam fingers 58B to apply a first lateral force to the first strain-sensing FBG 72, a second lateral force to the second strain-sensing FBG 24 and a third lateral force to the third strain-sensing FBG 76. In comparison to the first state of the reflected first, second and third Bragg wavelengths, a lateral force induced reflected first Bragg wavelength of the first strain-sensing FBG 72 is in a second state, shifted the same as or a different amount than a lateral force induced reflected second Bragg wavelength of the second FBG 74 in a third state, shifted the same as or a different amount than a lateral force induced reflected third Bragg wavelength of the third FBG 76 in a fourth state. The controller 46 is programmed use this Bragg wavelength shift information, compensated for by a change in the ambient temperature from the Bragg wavelength of the temperature-sensing FBG 77, to calculate the orientation in an x, y, z coordinate system of the atraumatic head 56 in the vasculature and the force that the atraumatic head is exerting against body tissue, for example, against an occlusion.

Thus, the controller 46 is programmed to detect and analyze the received Bragg wavelengths and output the precise orientation of the atraumatic head 56 in the vasculature on the display 78. In addition to calculating the orientation of the atraumatic head 56, the controller 46 is also programmed to analyze the detected Bragg wavelengths and output a precise reading related to the force that the atraumatic head 56 is exerting against vasculature tissue, and the like, during a medical procedure, such as identifying and treating an occlusion. That includes deciding whether to insert a stent, or not.

It is appreciated that various modifications to the inventive concepts described herein may be apparent to those of ordinary skill in the art without departing from the spirit and scope of the present invention as defined by the appended claims.

What is claimed is:

1. A guidewire assembly, comprising:
   a) a guidewire, comprising:
      i) a hypotube providing a lumen extending along a longitudinal axis from a hypotube proximal portion to a hypotube distal portion, the hypotube distal portion comprising a spring, wherein a hypotube lumen extends from the hypotube proximal portion to the hypotube distal portion;
      ii) a core wire residing in the hypotube lumen, the core wire extending from a core wire proximal end to a core wire distal end;
      iii) an atraumatic head connected to the hypotube distal portion;
      iv) an optical fiber supported by the core wire and extending through the hypotube lumen to the atraumatic head, wherein the optical fiber has at least a first fiber core comprising a first strain-sensing fiber Bragg grating (FBG) having a first Bragg wavelength, a second fiber core comprising a second strain-sensing FBG having a second Bragg wavelength, and a third fiber core comprising a third strain-sensing FBG having a third Bragg wavelength; and
      v) a collet residing in the hypotube lumen, wherein the collet is disposed between the atraumatic head and the optical fiber;
   b) at least one light source optically connected to the optical fiber, wherein the light source is configured:
      i) to emit light of a first spectrum into the first strain-sensing FBG, the first spectrum covering all possible reflection spectrum from the first FBG due to strain and temperature variations imparted to the first FBG;
      ii) to emit light of a second spectrum into the second strain-sensing FBG, the second spectrum covering all possible reflection spectrum from the second FBG due to strain and temperature variations imparted to the second FBG; and
      iii) to emit light of a third spectrum into the third strain-sensing FBG, the third spectrum covering all possible reflection spectrum from the third FBG due to strain and temperature variations imparted to the third FBG;
   c) a first light wavelength detector optically connected to the first fiber core, a second light wavelength detector optically connected to the second fiber core, and a third light wavelength detector optically connected to the third fiber core; and
   d) a controller operatively coupled to the first, second and third light wavelength detectors,
   e) wherein, with the at least one light source emitting the first light spectrum into the first FBG of the first fiber core, the second light spectrum into the second FBG of the second fiber core, and the third light spectrum into the third FBG of the third fiber core, and wherein, in comparison to a first state of the reflected first, second and third Bragg wavelengths with no axial force imparted to the atraumatic head, with an axial force being imparted to the atraumatic head to cause the atraumatic head to assume a neutral, unarticulated orientation axially aligned with the core wire, the atraumatic head applies equal radial pressure to the collet and the collet applies equal radial pressure to the first, second and third strain-sensing FBGs so that the reflected first, second and third Bragg wavelengths received by the respective first, second and third wavelength detectors are in a second state, shifted a similar amount with respect to the first state, and wherein the controller is programmed to use the difference between the first and second states to calculate the magnitude of the axial force vector imparted to the atraumatic head, and
   f) wherein, with a lateral force imparted to the atraumatic head to cause the atraumatic head and the spring of the distal hypotube portion to deflect out of axial alignment with the guidewire, the atraumatic head applies a lateral force to the collet to cause the collet to apply a first lateral force to the first FBG, a second lateral force to the second FBG and a third lateral force to the third FBG so that in comparison to the first state of the reflected first, second and third Bragg wavelengths, a lateral force induced reflected first Bragg wavelength of the first FBG is in a third state, shifted the same as or a different amount than a lateral force induced reflected second Bragg wavelength of the second FBG in a fourth state, shifted a different amount than a lateral force induced reflected third Bragg wavelength of the third FBG in a fifth state, and wherein the controller is programmed to use the differences in the third, fourth and fifth states of the lateral force induced reflected first, second and third Bragg wavelengths in comparison to the first state to calculate a lateral force magnitude and vector imparted to the atraumatic head.

2. The guidewire assembly of claim 1, wherein:
   a) the first optical fiber also comprises a fourth temperature-sensing FBG having a fourth Bragg wavelength, and
   b) the at least one light source is configured to emit light of a fourth spectrum into the fourth temperature-sensing FBG, the fourth spectrum covering all possible reflection spectrum from the fourth FBG due to temperature variations imparted to the fourth FBG, and
   c) a fourth wavelength detector is optically connected to the first optical fiber, and
   d) with the at least one light source emitting the fourth-light spectrum into the fourth FBG, the controller is operably coupled to the fourth wavelength detector and programmed to calculate a temperature induced shifted fourth Bragg wavelength as the difference between a sixth state of the reflected fourth Bragg wavelength of the fourth FBG at a first ambient temperature with the atraumatic head outside a body tissue in comparison to a seventh state of the reflected fourth Bragg wavelength of the fourth FBG at a second, local environment temperature with the atraumatic head inside a body tissue, and
   e) wherein the controller is further programmed to calculate for:
      i) the effect of the temperature induced shifted fourth Bragg wavelength on the reflected first, second and third Bragg wavelengths in the axial force induced second state to thereby determine a temperature-compensated magnitude of the axial force vector imparted to the atraumatic head, and ii) the effect of the temperature induced shifted fourth Bragg wavelength on the reflected first, second and third Bragg wavelengths in the respective lateral force induced third, fourth and fifth states to thereby determine a temperature-compensated lateral force magnitude and vector imparted to the atraumatic head as a result of the collet applying a greater lateral force to one of the first, second and third FBGs than the other FBGs.

3. The guidewire assembly of claim 2, wherein the first, second, third and fourth FBGs are individually selected from the group of a phase-shifted FBG, a long-period FBG, an apodized FBG, a chirped FBGs, and a tilted FBG.

4. The guidewire assembly of claim 1, wherein the first, second and third fiber cores are evenly spaced at 120° intervals in the optical fiber.

5. The guidewire assembly of claim 1, wherein the at least one light source is selected a Superluminescent light Emitting Diode (SLED) and a scanning laser.

6. The guidewire assembly of claim 1, wherein a first light source is optically connected to the first fiber core, a second light source is optically connected to the second fiber core, and a third light source is optically connected to the third fiber core.

7. The guidewire assembly of claim 6, wherein the first, second and third light sources are narrow linewidth lasers.

8. The guidewire assembly of claim 1, wherein the distal hypotube comprises a coil spring or a slotted spring.

9. The guidewire assembly of claim 1, wherein a proximal coil spring is supported on the core wire.

10. The guidewire assembly of claim 1, wherein a distal end of the optical fiber resides inside the atraumatic head.

11. The guidewire assembly of claim 1, wherein the atraumatic head, the first, second and third FBGs, the spring of the distal hypotube and the collet are radially aligned with each other.

12. The guidewire assembly of claim 1, wherein an optical connector optically connects the controller and an external optical fiber to the optical fiber of the guidewire.

13. The guidewire assembly of claim 12, wherein the optical connector has an electromechanical actuator, and wherein the controller is programmed to send a haptic vibration signal to the electromechanical actuator.

14. The guidewire assembly of claim 13, wherein the electromechanical actuator is selected from the group of a vibration motor, an eccentric rotating mass (ERM) actuator driven by an electronic circuit, a linear resonant actuator, and a piezoelectric actuator.

15. The guidewire assembly of claim 13, wherein the controller is programmed to increase a frequency or amplitude of the haptic vibration signal depending on the calculated temperature-compensated lateral force magnitude and vector imparted to the atraumatic head.

16. The guidewire assembly of claim 13, wherein the controller is programmed to vary a frequency of the haptic vibration signal to indicate a direction of the lateral force imparted to the atraumatic head.

17. The guidewire assembly of claim 13, wherein the controller is programmed to vary an amplitude of the haptic vibration signal to indicate the magnitude of the axial and lateral force vectors.

18. The guidewire assembly of claim 1, wherein the controller is further programmed to calculate an orientational value of the atraumatic head with respect to its axial alignment or non-alignment with the core wire from any one of:

a) the first state of the first, second and third Bragg wavelength with no axial pressure imparted to the atraumatic head;
b) the second state of the reflected first, second and third Bragg wavelengths with the axial pressure imparted to the atraumatic head; and
c) the lateral force induced reflected first Bragg wavelength of the first FBG in the third state, shifted the same as or a greater amount than the lateral force induced reflected second Bragg wavelength of the second FBG in the fourth state, shifted a greater amount than the lateral force induced reflected third Bragg wavelength of the third FBG in the fifth state.

19. A guidewire assembly, comprising:
a) a guidewire, comprising:
   i) a core wire extending from a core wire proximal end to a core wire distal end;
   ii) an intermediate hypotube connected to the core wire distal end;
   iii) a distal hypotube connected to the intermediate hypotube, wherein the distal hypotube comprises a spring;
   iv) an atraumatic head connected to the distal hypotube;
   v) an optical fiber extending from the core wire proximal end through the intermediate and distal hypotubes to the atraumatic head, wherein the optical fiber has at least a first fiber core comprising a first strain-sensing fiber Bragg grating (FBG) having a first Bragg wavelength, a second fiber core comprising a second strain-sensing FBG having a second Bragg wavelength, and a third fiber core comprising a third strain-sensing FBG having a third Bragg wavelength; and
   vi) a collet disposed between the atraumatic head and the optical fiber;
b) at least one light source optically connected to the optical fiber, wherein the light source is configured:
   i) to emit light of a first spectrum into the first strain-sensing FBG, the first spectrum covering all possible reflection spectrum from the first FBG due to strain and temperature variations imparted to the first FBG;
   ii) to emit light of a second spectrum into the second strain-sensing FBG, the second spectrum covering all possible reflection spectrum from the second FBG due to strain and temperature variations imparted to the second FBG; and
   iii) to emit light of a third spectrum into the third strain-sensing FBG, the third spectrum covering all possible reflection spectrum from the third FBG due to strain and temperature variations imparted to the third FBG;
c) a first light wavelength detector optically connected to the first fiber core, a second light wavelength detector optically connected to the second fiber core, and a third light wavelength detector optically connected to the third fiber core; and
d) a controller operatively coupled to the first, second and third light wavelength detectors,
e) wherein, with the at least one light source emitting the first light spectrum into the first FBG of the first fiber core, the second light spectrum into the second FBG of the second fiber core, and the third light spectrum into the third FBG of the third fiber core, and wherein, in comparison to a first state of the reflected first, second and third Bragg wavelengths with no axial force imparted to the atraumatic head, with an axial force imparted to the atraumatic head to cause the atraumatic head to assume a neutral, unarticulated orientation axially aligned with the core wire, the atraumatic head applies equal radial pressure to the collet and the collet applies equal radial pressure to the first, second and third strain-sensing FBGs so that the reflected first, second and third Bragg wavelengths received by the respective first, second and third wavelength detectors are in a second state, shifted a similar amount with respect to the first state, and wherein the controller is programmed to use the difference between the first and second states to calculate the magnitude of the axial force vector imparted to the atraumatic head, and f) wherein, with a lateral force imparted to the atraumatic head to cause the atraumatic head and the spring of the distal hypotube to deflect out of axial alignment with the core wire, the atraumatic head applies a lateral force to the collet to cause the collet to apply a first lateral force to the first FBG, a second lateral force to the second FBG and a third lateral force to the third FBG so that in comparison to the first state of the reflected first, second and third Bragg wavelengths, a lateral force induced reflected first Bragg wavelength of the first FBG is in the third state, shifted the same as or a different amount than a lateral force induced reflected second Bragg wavelength of the second FBG in the fourth state, shifted a different amount than a lateral force induced reflected third Bragg wavelength of the third FBG in a fifth state, and wherein the controller is programmed to use the differences in the third, fourth and fifth states of the lateral force induced reflected first, second and third Bragg wavelengths in comparison to the first state to calculate a lateral force magnitude and vector imparted to the atraumatic head.

20. A guidewire assembly, comprising:
a) a guidewire, comprising:
  i) a hypotube providing a lumen extending along a longitudinal axis from a hypotube proximal portion to a hypotube distal portion, the hypotube distal portion comprising a spring, wherein a hypotube lumen extends from the hypotube proximal portion to the hypotube distal portion;
  ii) an atraumatic head connected to the hypotube distal portion;
  iii) an optical fiber extending through the hypotube lumen to the atraumatic head, wherein the optical fiber has at least a first fiber core comprising a first strain-sensing fiber Bragg grating (FBG) having a first Bragg wavelength, a second fiber core comprising a second strain-sensing FBG having a second Bragg wavelength, and a third fiber core comprising a third strain-sensing FBG having a third Bragg wavelength; and
  iv) a collet residing in the hypotube lumen, wherein the collet is disposed between the atraumatic head and the optical fiber;
b) at least one light source optically connected to the optical fiber, wherein the light source is configured:
  i) to emit light of a first spectrum into the first strain-sensing FBG, the first spectrum covering all possible reflection spectrum from the first FBG due to strain and temperature variations imparted to the first FBG;
  ii) to emit light of a second spectrum into the second strain-sensing FBG, the second spectrum covering all possible reflection spectrum from the second FBG due to strain and temperature variations imparted to the second FBG; and
  iii) to emit light of a third spectrum into the third strain-sensing FBG, the third spectrum covering all possible reflection spectrum from the third FBG due to strain and temperature variations imparted to the third FBG;
c) a first light wavelength detector optically connected to the first fiber core, a second light wavelength detector optically connected to the second fiber core, and a third light wavelength detector optically connected to the third fiber core; and
d) a controller operatively coupled to the first, second and third light wavelength detectors,
e) wherein, with the at least one light source emitting the first light spectrum into the first FBG of the first fiber core, the second light spectrum into the second FBG of the second fiber core, and the third light spectrum into the third FBG of the third fiber core, and wherein, in comparison to a first state of the reflected first, second and third Bragg wavelengths with no axial force imparted to the atraumatic head, with an axial force imparted to the atraumatic head to cause the atraumatic head to assume a neutral, unarticulated orientation axially aligned with the longitudinal axis, the atraumatic head applies equal radial pressure to the collet and the collet in turn applies equal radial pressure to the first, second and third strain-sensing FBGs so that the reflected first, second and third Bragg wavelengths received by the respective first, second and third wavelength detectors are in a second state, shifted a similar amount with respect to the first state, and wherein the controller is programmed to use the difference between the first and second states to calculate the magnitude of the axial force vector imparted to the atraumatic head, and f) wherein, with a lateral force imparted to the atraumatic head to cause the atraumatic head and the spring of the hypotube to deflect out of axial alignment with the longitudinal axis, the atraumatic head applies a lateral force to the collet to cause the collet in turn to apply a first lateral force to the first FBG, a second lateral force to the second FBG and a third lateral force to the third FBG so that in comparison to the first state of the reflected first, second and third Bragg wavelengths, a lateral force induced reflected first Bragg wavelength of the first FBG is in a third state, shifted the same as or a different amount than a lateral force induced reflected second Bragg wavelength of the second FBG in a fourth state, shifted a different amount than a lateral force induced reflected third Bragg wavelength of the third FBG in a fifth state, and wherein the controller is programmed to use the differences in the third, fourth and fifth states of the lateral force induced reflected first, second and third Bragg wavelengths in comparison to the first state to calculate a lateral force magnitude and vector imparted to the atraumatic head.

21. The guidewire assembly of claim 20, wherein an optical connector optically connects the controller and an external optical fiber to the optical fiber of the guidewire.

22. The guidewire assembly of claim 21, wherein the optical connector has an electromechanical actuator, and wherein the controller is programmed to send a haptic feedback signal to the electromechanical actuator.

* * * * *